United States Patent
Thompson et al.

(10) Patent No.: US 6,830,569 B2
(45) Date of Patent: Dec. 14, 2004

(54) ELECTROSURGICAL GENERATOR AND METHOD FOR DETECTING OUTPUT POWER DELIVERY MALFUNCTION

(75) Inventors: Richard Thompson, Centennial, CO (US); Tim Refior, Parker, CO (US)

(73) Assignee: ConMed Corporation, Utica, NY (US)

( * ) Notice: Subject to any disclaimer, the term of this patent is extended or adjusted under 35 U.S.C. 154(b) by 80 days.

(21) Appl. No.: 10/300,703

(22) Filed: Nov. 19, 2002

(65) Prior Publication Data

US 2004/0097916 A1 May 20, 2004

(51) Int. Cl.[7] .............................................. A61B 18/18
(52) U.S. Cl. ......................................... 606/34; 606/42
(58) Field of Search ......................... 606/32–34, 37–42

(56) References Cited

U.S. PATENT DOCUMENTS

| | | | |
|---|---|---|---|
| 1,863,118 A | 6/1932 | Liebel | |
| 3,252,052 A | 5/1966 | Nash | |
| 3,683,923 A | 8/1972 | Anderson | |
| 3,963,030 A | 6/1976 | Newton | |
| 4,094,320 A | 6/1978 | Newton et al. | |
| 4,171,700 A | * 10/1979 | Farin | 606/35 |
| 4,231,372 A | 11/1980 | Newton | |
| 4,237,887 A | 12/1980 | Gonser | |
| 4,416,276 A | 11/1983 | Newton et al. | |
| 4,416,277 A | 11/1983 | Newton et al. | |
| 4,488,057 A | 12/1984 | Clarke | |
| 4,658,815 A | * 4/1987 | Farin et al. | 606/34 |
| 4,716,897 A | 1/1988 | Noguchi et al. | |
| 4,739,759 A | * 4/1988 | Rexroth et al. | 606/37 |
| 4,751,371 A | 6/1988 | Clinton | |
| 4,848,335 A | 7/1989 | Manes | |
| 4,860,745 A | 8/1989 | Farin et al. | |
| 5,019,076 A | 5/1991 | Yamanashi et al. | |
| 5,190,517 A | 3/1993 | Zieve et al. | |
| 5,300,070 A | 4/1994 | Gentelia et al. | |
| 5,575,789 A | 11/1996 | Bell et al. | |
| 5,599,344 A | 2/1997 | Paterson | |
| 5,772,659 A | 6/1998 | Becker et al. | |
| 5,830,212 A | 11/1998 | Cartmell et al. | |
| 6,033,399 A | 3/2000 | Gines | |
| 6,113,596 A | 9/2000 | Hooven et al. | |
| 6,251,106 B1 | 6/2001 | Becker et al. | |
| 6,652,514 B2 | * 11/2003 | Ellman et al. | 606/37 |
| 6,679,875 B2 | * 1/2004 | Honda et al. | 606/1 |

FOREIGN PATENT DOCUMENTS

| | | | |
|---|---|---|---|
| EP | 1050277 | | 11/2000 |
| GB | 2154881 | * | 9/1985 |

OTHER PUBLICATIONS

H. Hölscher et al., *Microcomputers in Safety Technique, An Aid to Orientation for Developer and Manufacturer*, 1986, Chapter 1–1 through 8–9.

International Search Report for the PCT application PCT/US 03/33786 which corresponds to the present U.S. application.

Eggleston; patent application Publication U.S. 2001/0031962 A1; Oct. 18, 2001.

* cited by examiner

*Primary Examiner*—Michael Peffley
(74) *Attorney, Agent, or Firm*—John R. Ley (57) ABSTRACT

Output power delivery from an electrosurgical generator is evaluated to avoid malfunctions and risk conditions. Output power is delivered in a selected delivery path and the flow of output power is sensed in the selected delivery path and other delivery paths which have not been selected. The output power delivery is terminated upon determining that output power is not flowing in the selected delivery path or that output power is flowing in a delivery path that was not selected.

21 Claims, 4 Drawing Sheets

ELECTROSURGICAL GENERATOR AND METHOD FOR DETECTING OUTPUT POWER DELIVERY MALFUNCTION

FIELD OF THE INVENTION

This invention generally relates to electrosurgery. More specifically, the invention relates to a new and improved electrosurgical generator and method that has the capability to detect malfunctions or errors in the delivery or distribution of high power electrosurgical energy to one or more electrosurgical instruments connected to the generator, thereby indicating and preventing malfunctions and error conditions which could possibly result in an unintended application of electrosurgical energy to a patient or to surgical personnel.

BACKGROUND OF THE INVENTION

Electrosurgery involves applying relatively high voltage, radio frequency (RF) electrical energy to tissue of a patient undergoing surgery, for the purpose of cutting the tissue, coagulating or stopping blood or fluid flow from the tissue, or cutting and coagulating the tissue simultaneously. The high voltage, RF electrical energy is created by an electrosurgical generator, and the electrical energy from the generator is applied to the tissue from an instrument or handpiece manipulated by a surgeon during the surgical procedure.

In monopolar electrosurgery, the handpiece includes a single active electrode. The active electrode is applied to the tissue, and the electrical energy travels from the generator, through a conductor to the handpiece, from the active electrode of the handpiece into the tissue of the patient, where the cutting, coagulating or simultaneous cutting and coagulating effect is achieved at the interface of the active electrode with the tissue. The electrical current is distributed into the patient, collected from the patient by a return electrode connected to the patient at a location remote from the surgical site, and is returned to the electrosurgical generator by an electrical conductor connected to the return electrode.

In bipolar electrosurgery, the handpiece generally takes the form of a forceps. The active electrode and the return electrode are attached at opposite ends of the arms of the forceps. Tissue is grasped between the active and return electrodes and the electrosurgical energy is transferred directly between the active and return electrodes through the tissue. Bipolar electrosurgery is generally used only for coagulating tissue, such as by squeezing a severed vessel and applying the electrosurgical energy to seal the end of the severed vessel.

Frequently, a surgeon will use different monopolar and bipolar handpieces on an alternating basis during the course of the surgical procedure. For example, the surgeon may use a monopolar handpiece having a relatively straight active electrode for cutting, another monopolar handpiece having a different configuration of an active electrode for coagulating broad surfaces of oozing tissue, and bipolar forceps for coagulating blood flow from severed vessels. In some complex surgical procedures, two or more surgeons may perform a procedure on the same patient at the same time, but at different surgical sites. For example, in a heart bypass operation, one surgeon may be working at the thoracic cavity while another surgeon may be harvesting vessel tissue from a leg. In this situation, each surgeon will typically use a handpiece or handpieces separate from those used by the other surgeon.

In all of these situations, it is typical that the multiple handpieces are connected to a single electrosurgical generator. The surgeon controls the energy delivered to the selected handpiece by depressing a finger switch on the handpiece, or by stepping on a foot switch which is associated with the particular handpiece. Depressing a finger switch or stepping on a foot switch delivers an activation signal to the electrosurgical generator. The electrosurgical generator responds to the activation signal by delivering the electrosurgical energy to the handpiece with which the activation signal is associated. Most electrosurgical generators contain the capability of delivering monopolar electrosurgical energy to more than one connected handpiece, so relays are used to direct the high power electrosurgical energy only to the desired handpiece. Relays are used because the electrosurgical energy can be of high voltage, for example up to 10,000 volts, making it extremely difficult or impossible to use non-mechanical electrical switches for this purpose.

After many repeated openings and closures, an output relay of an electrosurgical generator can become worn, just like any other mechanical device which is subjected to repeated use. Sometimes a worn or defective output relay will not close when commanded to do so. In such circumstances, the electrosurgical energy will not be delivered to the handpiece and the surgeon quickly recognizes a malfunction of the electrosurgical generator. Sometimes a worn output relay will stick in the closed position. While an output relay that is stuck in the closed position may not be particularly problematic when only a single handpiece is connected to the electrosurgical generator, this is not the case when multiple handpieces are connected to the same generator.

An activation request for bipolar energy is interpreted by the electrosurgical generator to connect the necessary electrical components for delivering the electrosurgical energy directly to the bipolar forceps.

An output relay that is stuck in the closed position can deliver electrosurgical energy to its associated handpiece, even if that particular handpiece has not been selected by an activation request. The delivery of electrosurgical energy to an unintended handpiece can result in injury to the patient and to the surgical personnel. In some situations, the surgeon will lay the handpiece on the patient when the handpiece is not in use, simply because it is convenient to pick up the handpiece when the procedure requires the application of electrosurgical energy. In other cases, the surgeon may pass the handpiece to surgical support personnel who will hold the handpiece until the surgeon requires it, or the surgeon may hold or use the handpiece in a way that is safe so long as electrosurgical energy is not delivered from it. In all of these cases, if the active electrode of the handpiece becomes energized by a stuck output relay, there is a possibility of an unintended burn, injury or electrical shock to the patient, the surgeon or the surgical personnel. Moreover, there is also a possibility that an electrical short-circuit could be established through the generator, which would disable the generator and prevent its use for the remainder of the procedure. Under those circumstances, the procedure must be suspended while a replacement electrosurgical generator is located and brought into the operating room. Bipolar electrosurgical energy is typically delivered through different output electrical components from those that are connected in the output circuit of the electrosurgical generator when monopolar electrical energy is delivered. Because of the separate electrical delivery of bipolar ehectrosurgical energy, output relays may or may not be used to connect the bipolar electrosurgical energy to the bipolar handpieces. The misinterpretation of a bipolar activation request may erroneously deliver bipolar electrosurgical power to the bipolar handpiece.

SUMMARY OF THE INVENTION

In accordance with the improvements of the present invention, the operational condition and status of an output relay and the bipolar output delivery circuitry of an electrosurgical generator is detected and evaluated in response to activation requests. Evaluating the delivery of electrosurgical energy relative to expected conditions arising from the activation request detects a malfunction or error condition of an output relay or in the electrical components which deliver bipolar energy. Detecting a malfunction, and preventing the delivery of electrosurgical power under such conditions, avoids or minimizes the risk of unintentional injury, burns or electrical shock to the patient, the surgeon or the surgical personnel. The opportunity to assist in troubleshooting or identifying intermittently malfunctioning output relays or other internal malfunctions within the electrosurgical generator is also achieved from the present invention.

The invention involves a method of determining delivery conditions of output electrosurgical power from an electrosurgical generator. The electrosurgical power is delivered in response to an activation request for output power. A delivery path for the delivery of the electrosurgical power is selected based on the activation request. A determination is made whether the output power delivered is flowing in any delivery path other than the selected delivery path. The delivery of electrosurgical power is terminated upon determining that the delivered electrosurgical output power is flowing in a delivery path other than the selected delivery path. Preferably, a determination is also made whether the electrosurgical output power delivered is flowing in the selected delivery path, and the delivery of the electrosurgical power is terminated upon determining that output power is flowing in a delivery path other than the selected delivery path. The delivery path is preferably a selected one of a plurality of different delivery paths.

Another form of the invention involves delivering electrosurgical power in response to an activation request, commanding the delivery of electrosurgical power through a selected one of a plurality of delivery paths, sensing the flow of electrosurgical power in each of the plurality of delivery paths, determining whether the delivery path in which electrosurgical power is flowing correlates with the selected one delivery path and whether each delivery path in which electrosurgical power is not flowing correlates to a delivery path for which electrosurgical power delivery has not been commanded, and terminating the delivery of electrosurgical power if electrosurgical power is not flowing in the selected delivery path or if electrosurgical power is flowing in any delivery path other than the selected one delivery path.

The invention also involves an improved electrosurgical generator. The electrosurgical generator comprises a power creation circuit which is operative in response to an enable signal to create the output electrosurgical energy, a delivery path connected to the power creation circuit and through which the output electrosurgical energy is delivered, a selectively controllable power flow switch connected in the delivery path to conduct the electrosurgical energy through the delivery path in response to an assertion of a power command signal to the power flow switch and to prevent conduction of the electrosurgical power through the delivery path in response to the de-assertion of the power command signal, a controller receptive of an activation signal to the electrosurgical generator and operative to supply the enable signal to the power creation circuit and to assert the command signal to the power flow switch in response to the activation signal, a sensor connected to sense the flow of electrosurgical power through the delivery path and to assert a sense signal upon sensing the presence of electrosurgical energy flowing in the delivery path and to de-assert the sense signal upon sensing the absence of electrosurgical energy flowing in the delivery path, and a detection circuit receptive of the command signal and the sense signal and responsive to an inconsistency in one of the simultaneous assertions of the command and sense signals or the simultaneous de-assertion of the command and sense signals. The detection circuit terminates the enable signal to the power creation circuit upon detecting the inconsistency.

A more complete appreciation of the present disclosure and its scope, and the manner in which it achieves the above noted improvements, can be obtained by reference to the following detailed description of presently preferred embodiments taken in connection with the accompanying drawings, which are briefly summarized below, and the appended claims.

DETAILED DESCRIPTION

Figure 1:
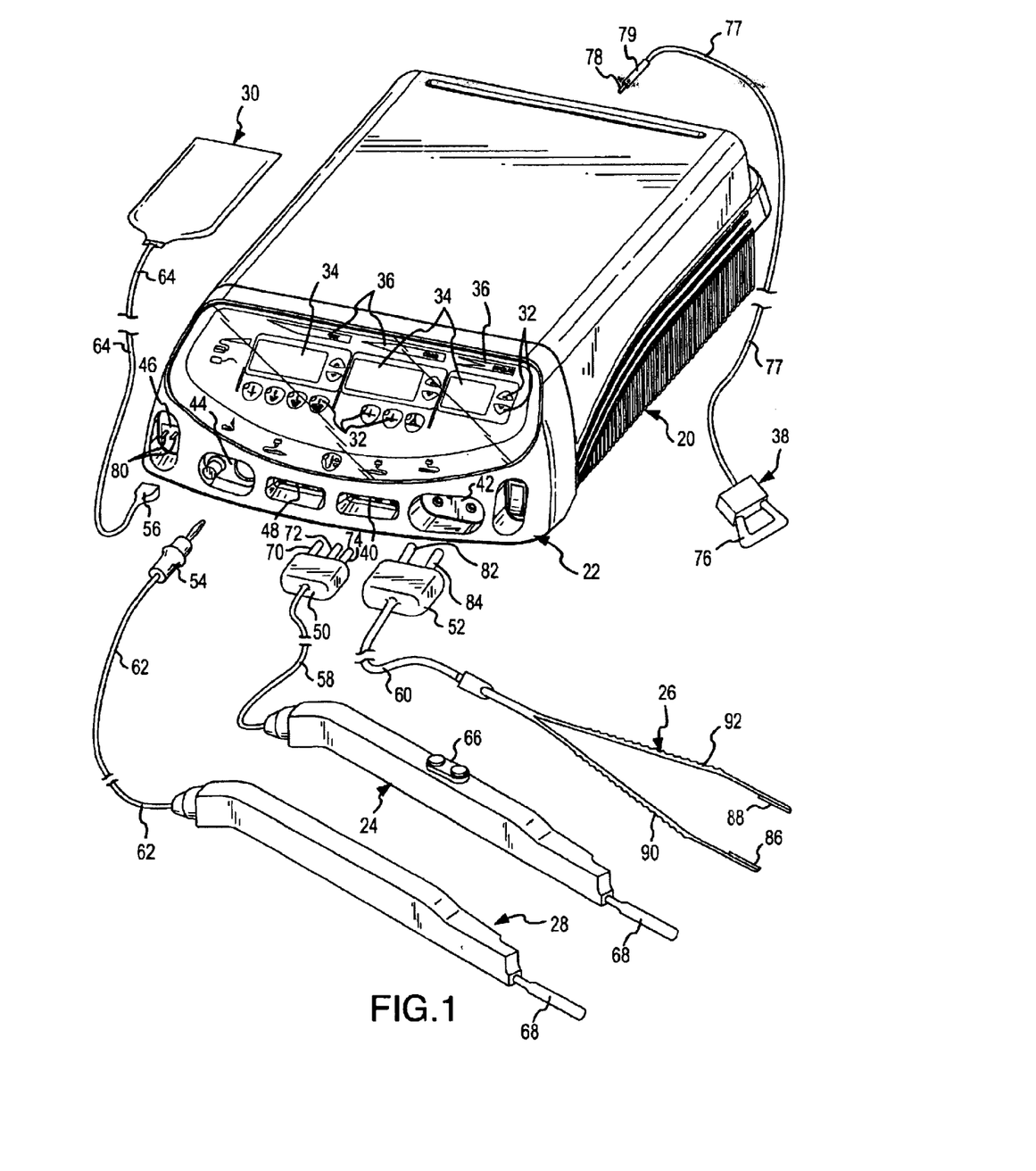
FIG. 1 is a perspective view of an electrosurgical generator which incorporates the present invention, and a typical finger-switched monopolar electrosurgical handpiece, a typical foot-switched monopolar electrosurgical handpiece, a typical bipolar electrosurgical handpiece, a typical foot switch, and a typical return electrode, all of which may be connected to the electrosurgical generator.

An electrosurgical generator 20, shown in FIG. 1, includes a front panel 22 at which to connect various conventional electrosurgical instruments and accessories, including a finger-switched monopolar handpiece 24, a bipolar handpiece or forceps 26, a foot-switched monopolar handpiece 28, and a return electrode 30. The front panel 22 also includes various touch input switch devices 32, displays 34 and indicators 36, which are used to control the operation of the electrosurgical generator by setting cut, coagulation or simultaneous cut and coagulation modes of electrosurgical operation and the amount of electrosurgical power to be delivered in the selected mode of operation, among other typical things. The front panel 22 functions as a user interface for the electrosurgical generator 20 with regard to performing input/output tasks. A typical foot switch 38 is also connected to the electrosurgical generator 20, at a back or rear housing panel (not visible in FIG. 1).

The front panel 22 locates and positions various electrical connector plug-receiving receptacles 40, 42, 44 and 46 by which to electrically connect the finger-switched monopolar handpiece 24, the bipolar forceps 26, the foot-switched monopolar handpiece 28 and the return electrode 30, respectively. The front panel 22 also includes another electrical connector plug-receiving receptacle 48 by which to connect an additional finger-switched monopolar handpiece (not shown) similar to the one handpiece 24 shown. The finger-switched monopolar handpiece 24, the bipolar forceps 26, the foot-switched monopolar handpiece 28 and the return electrode 30 each include an electrical connector plug 50, 52, 54 and 56 which is inserted into the plug-receiving receptacles 40, 42, 44 and 46 when connecting the finger-switched monopolar handpiece 24, the bipolar forceps 26, the foot-switched monopolar handpiece 28 and the return electrode 30 to the electrosurgical generator 20, respectively. The connector plugs 50, 52, 54 and 56 are electrically connected by conductors 58, 60, 62 and 64 to the finger-switched monopolar handpiece 24, the bipolar forceps 26, the foot-switched monopolar handpiece 28 and the return electrode 30, respectively.

The typical finger-switched monopolar handpiece 24 includes a finger activation switch 66 for the surgeon to depress to activate the electrosurgical generator 20 to deliver electrosurgical power from the plug-receiving receptacle 40 (or 48), to the connector plug 50, through the conductors 58 to the handpiece 24, and from an active electrode 68 connected at the distal end of the handpiece 24. One prong 70 of the connector plug 50 conducts the high voltage RF electrosurgical power through one of the conductors 58 to the active electrode 68. Two other prongs 72 and 74 of the connector plug 50 conduct activation signals from the activation switch 66 through the conductors 58 to the electrosurgical generator 20. The prong 72 conducts an activation signal from the finger switch 66 indicating that coagulation mode power is to be delivered to the active electrode 68, and the prong 74 conducts an activation signal from the finger switch 66 indicating that cut mode power is to be delivered to the active electrode 68.

The foot-switched monopolar handpiece 28 is similar to the finger-switched monopolar handpiece 24, except that the foot-switched monopolar handpiece 28 does not include a finger switch 66 to activate the electrosurgical generator 20. Instead, the foot-switched monopolar handpiece 28 requires the use of the foot switch 38 to activate the electrosurgical generator 20. The foot switch 38 includes a pedal 76 which is depressed by the foot of the surgeon, and in response, the foot switch 38 delivers an activation signal through conductors 77 to a prong 78 of a foot switch connector plug 79. In response to the activation signal from the foot switch 38, the electrosurgical generator 20 is activated and delivers electrosurgical power through the plug-receiving receptacle 44 into which is the electrical connector plug 54 of the foot-switched monopolar handpiece 28 is connected.

An electrical circuit for monopolar current flow from the active electrode 68 through the patient is established by connecting the return electrode 30 to the skin of the patient at a location remote from the surgical site. The electrical current is collected from the patient's body by the return electrode 30, conducted through the conductors 64 and returned to the electrosurgical generator through connector plug 56 which is inserted into the plug-receiving receptacle 46. The plug receiving receptacle 46 for connecting the return electrode 30 includes a pair of male prongs 80 which extend into female sockets (not shown) of the connector plug 56.

Electrical energy for bipolar electrosurgery performed with the bipolar forceps 26 is delivered from the plug-receiving receptacle 42 and conducted through prongs 82 and 84 of the connector plug 52. The electrosurgical energy is conducted from the plug-receiving receptacle 42 and into the prongs 82 and 84 of the connector plug 52, through the conductors 60 and delivered to electrodes 86 and 88 connected at the distal ends of arms 90 and 92 of the forceps 26. One of the electrodes 86 or 88 transfers current into the tissue confined between the two electrodes 86 and 88 by squeezing the arms 90 and 92 and the other electrode 86 or 88 collects and returns the current from the tissue. In bipolar electrosurgery, the electrosurgical current flows directly between the electrodes 86 and 88, making the use of the return electrode 30 unnecessary. The electrosurgical generator is typically activated to deliver the bipolar electrosurgical energy to the forceps 26 by depressing the pedal 76 of the foot switch 38, in the same manner as has been as has been described for activating the foot-switched monopolar handpiece 28. Some types of bipolar forceps 26 include a switch which generates an activation signal upon squeezing the arms 90 and 92 together.

The present invention correlates the activation signals with a signal indicating current flow to the receptacles 40, 42, 44 and 48. This correlation determines whether a malfunction has occurred in the distribution of the electrosurgical energy. Such a malfunction could occur from a stuck-closed output relay which is distributing the electrosurgical current to a handpiece for which an activation request was not made. Such a malfunction could also occur from a stuck-open output relay which prevents electrosurgical current from flowing to a handpiece for which an activation request was made. Another type of malfunction might arise from the distribution of electrosurgical current to the bipolar receptacle 42 when it should have been delivered to a monopolar receptacle 40, 44 or 48, or vice versa. Moreover, combinations of these malfunction can be detected.

In response to the detection of a malfunction in the distribution of the electrosurgical energy from the electrosurgical generator, further power delivery is terminated. In general, the improvements of the present invention permit the output power delivery characteristics of the electrosurgical generator to be monitored and controlled to prevent or reduce risks of injury to the patient and the surgical personnel. The present invention is also useful in identifying malfunctions for purposes of quickly correcting them in maintenance operations.

Figure 2:
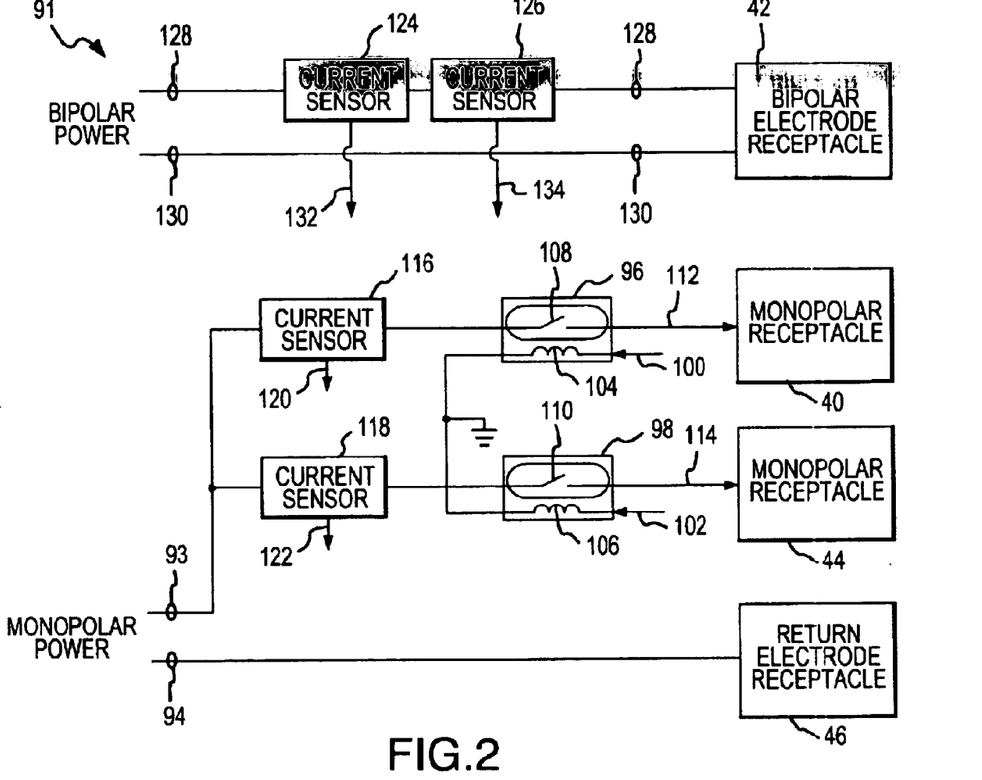
FIG. 2 is a block and schematic diagram of an electrosurgical power distribution circuit of the electrosurgical generator shown in FIG. 1, which conducts electrosurgical output power to the monopolar electrosurgical handpiece, the bipolar electrosurgical handpiece and the return electrode shown in FIG. 1.

In order to detect output power distribution malfunctions, the monopolar and bipolar electrosurgical energy delivered by the electrosurgical generator 20 is distributed to the monopolar handpiece 24 and 28 and to the bipolar forceps 26 through an output power distribution circuit 91, shown in FIG. 2. Monopolar electrosurgical energy is applied to a monopolar active conductor 93 and a monopolar return conductor 94. The return conductor 94 is connected to the receptacle 46 to which the plug connector 56 of the return electrode 30 is connected. Conductor 94 therefore conducts the return current from the return electrode back to the electrosurgical generator.

Active monopolar current is supplied to the conductor 93. The current on conductor 93 ultimately flows to the active electrode 68 of one of the monopolar handpieces 24 or 28 (FIG. 1). The active monopolar electrosurgical current is conducted to the monopolar handpiece 24 or 28 through a closed high-voltage output relay 96 and 98, only one of which is closed at a time under proper operating conditions. Each high-voltage output relay 96 or 98 is closed by the application of a relay closure signal 100 and 102 applied to the relays 96 and 98, respectively. Upon application of a relay closure signal 100 or 102, a conventional coil 104 or 106 of the relay 96 or 98 is energized to close a switch 108 or 110, respectively. When the relay closure signal 100 or 102 is not applied, the switch 108 or 110 should be opened and therefore nonconductive if the relay 96 or 98 is operating properly. The electrosurgical current conducted through the closed relays 96 and 98 is applied to conductors 112 and 114. The conductors 112 and 114 are connected to the receptacles 40 and 44 (FIG. 1). The connection to the monopolar receptacle 48 (FIG. 1) is similar to that shown with respect to receptacle 40 and is therefore not duplicated in FIG. 2. The electrosurgical current flows from each conductor 112 and 114 to the plug connector 50 or 54 of the monopolar handpieces 24 or 28 connected to the receptacles 40 or 44. The electrosurgical current from conductors 112 and 114 is ultimately conducted to the active electrode 68 of the monopolar handpieces (FIG. 1).

Current sensors 116 and 118 are connected between the conductor 93 and the relays 96 and 98, respectively. The current sensors 116 and 118 supply current sense signals 120 and 122, indicating the presence of current flow when the relays 96 and 98 are closed, respectively. The current sense signals 120 and 122 are correlated to the relay closure signals 100 and 102. By comparing the relay closure signals 100 and 102, or the activation signals which should have resulted in the relay closure signals 100 and 102, with the current sense signals 120 and 122, it is determined whether the output relay 96 or 98 has been properly closed and whether any other output relay 96 or 98 which should not have been closed is erroneously closed. Upon recognizing any such malfunction condition, the electrosurgical output power is terminated.

A related output power distribution detection capability exists with respect to the delivery of bipolar electrosurgical power. In the case of bipolar energy delivery, current sensors 124 and 126 are connected to sense bipolar current flow through the conductor 128. In some types of electrosurgical generators, there are no output relays in the bipolar electrosurgical current path, because those types of electrosurgical generators have only one receptacle 42 (FIG. 1) for the delivery of bipolar electrosurgical power and because the bipolar electrosurgical output power is generated by electrical circuit components that are different from those used for generating the monopolar electrosurgical output power. The current sensors 124 and 126 supply current sense signals 132 and 134 in response to detecting current flow in the conductor 128. By comparing the bipolar activation request signal with the current sense signals 132 and 134, it is determined whether bipolar current is properly and improperly delivered. If current is detected by one sensor 124 or 126 and not by the other sensor, a malfunction is indicated.

Moreover, by comparing the presence and absence of the bipolar current sense signals 132 and 134 with the presence and absence of the monopolar current sense signals 120 and 122, and by comparing all of the current sense signals 120, 122, 132 and 134 with the activation request signals to the electrosurgical generator and the relay activation signals 112 and 114 generated in response to the activation request signals, it is determined whether the electrosurgical output power distribution of the electrosurgical generator is proper.

Figure 3:
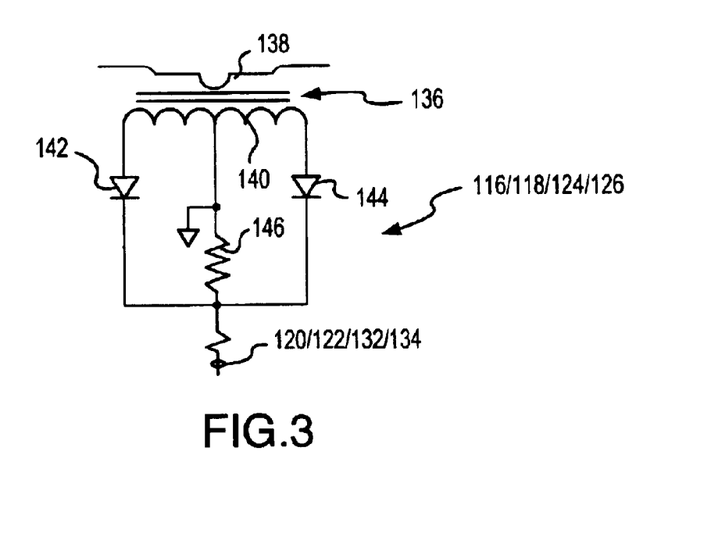
FIG. 3 is a simplified circuit diagram of a current sensor shown in FIG. 2.

Each of the current sensors 116, 118, 124 and 126 preferably takes the form shown in FIG. 3. A transformer 136 has a primary winding 138 which conducts the electrosurgical current distributed from the electrosurgical generator. The current through the primary winding 138 is alternating current (AC) because the electrosurgical current is applied as radio frequency (RF). An AC signal is inductively coupled into a secondary winding 140 of the transformer 136, and that AC signal is rectified by diodes 142 and 144. A resistor 146 establishes a value for the rectified AC signal, and that signal is supplied as the current sense signal 120, 122, 132, or 134.

Figure 4:
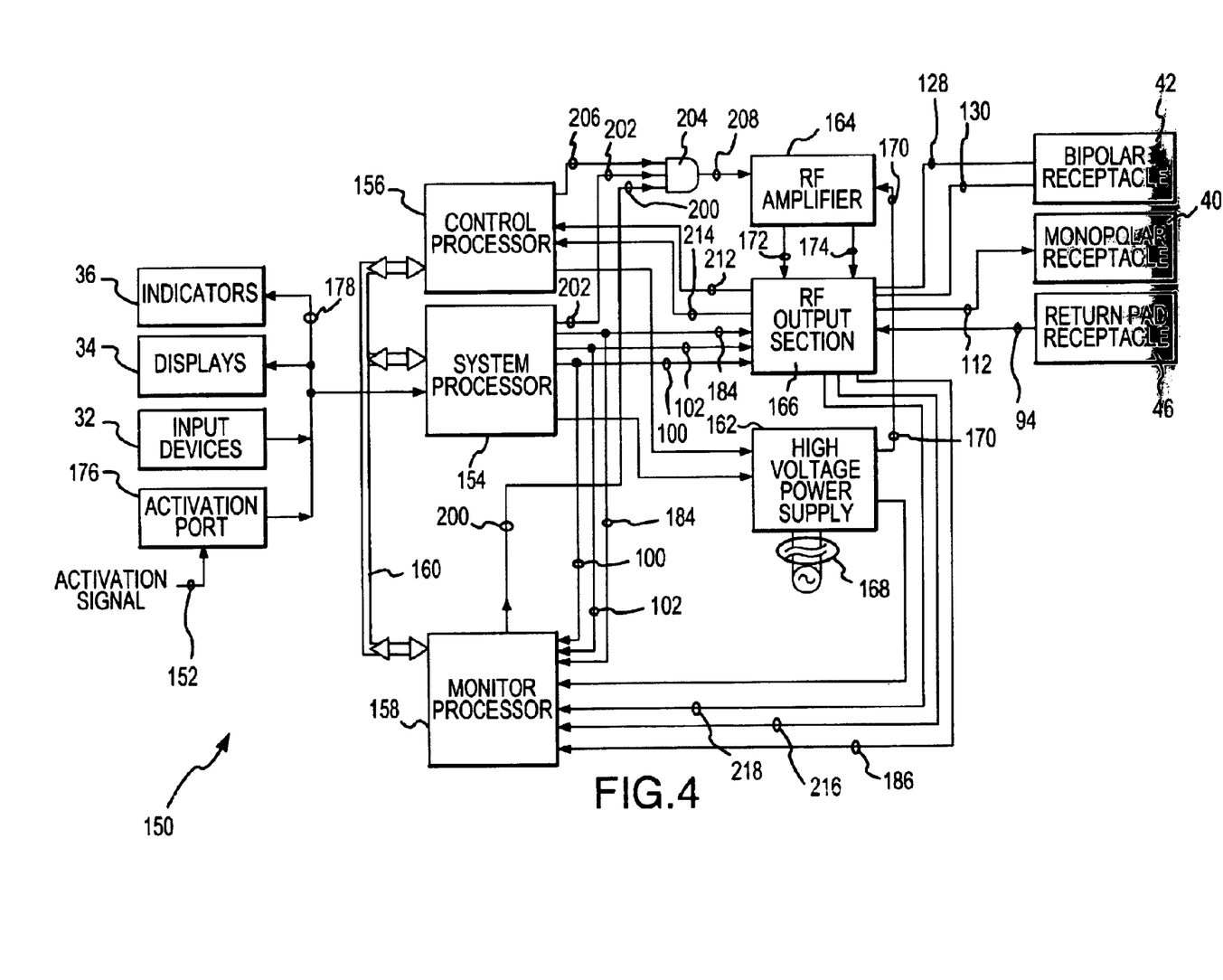
FIG. 4 is a block diagram of general electrical components of the electrosurgical generator shown in FIG. 1, of which the power distribution circuit shown in FIG. 2 is a part.

To detect and respond to output power distribution malfunctions of the generator, the electrosurgical generator 20 (FIG. 1) includes electrical components 150, preferably organized as shown in FIG. 4. Bipolar electrosurgical power is supplied on conductors 128 and 130 to the bipolar receptacle 42. Active monopolar electrosurgical current is supplied on conductor 112 to the monopolar receptacle 40. The other monopolar receptacles 44 and 48 (FIG. 1) are not shown in FIG. 4, but they connected in a manner similar to the monopolar receptacle 40. Return monopolar electrosurgical current is received at the return electrode receptacle 46 and supplied to the electrical components 150 on the conductor 94. The electrosurgical generator is activated to deliver the electrosurgical output power by an activation signal 152 supplied by either the finger switch 66 of the monopolar handpiece 24 (FIG. 1) or by the foot switch 38 (FIG. 1).

The generator components 150 include a system processor 154, a control processor 156, and a monitor processor 158. The system processor 154 generally controls the overall functionality of the generator components 150. The system processor 154 includes nonvolatile memory (not shown) containing programmed instructions to download to the other processors 156 and 158 to establish the functionality of the control and monitor processors 156 and 158. The processors 154, 156 and 158 communicate with each other over a system bus 160. In general, the system processor 154 supervises and controls, at a high level, the entire functionality of the electrical generator components 150.

The primary functionality of the control processor 156 is to establish and regulate the output power delivered. The control processor 156 is connected to a high voltage power supply 162, an RF amplifier 164, and an RF output section 166. The high voltage power supply 162 generates a DC operating voltage 170 by rectifying conventional alternating current (AC) power supplied by conventional mains power lines 168, and delivers the DC operating voltage power to the RF amplifier 164 at 170. The RF amplifier 164 converts the DC operating voltage 170 into monopolar drive signals 172 and bipolar drive signals 174 having an energy content and duty cycle appropriate for the amount of power and the mode of electrosurgical operation which have been selected by the surgeon. The RF output section 166 converts the monopolar and bipolar drive signals 172 and 174 into the RF voltage and current waveforms appropriate to the monopolar and bipolar mode of operation selected for the electrosurgical generator, and supplies those waveforms to the monopolar receptacle 40 and the bipolar receptacle 42. The RF output section 166 also includes the power distribution circuit 91 shown in FIGS. 2 and 3.

The basic function of the monitor processor 158 is to monitor the functionality of the high voltage power supply 162 and the RF output section 166, as well as to monitor the functions of the system processor 154 and the control processor 156. If the monitor processor 158 detects a discrepancy in the output electrosurgical energy, or a discrepancy in the distribution of the output electrosurgical energy, or a discrepancy in the expected functionality of the system processor 154 or the control processor 156, a failure or error mode is indicated. Under such circumstances, the monitor processor 158 terminates the delivery of output electrosurgical energy from the generator components 150 to the monopolar receptacle 40 and the bipolar receptacle 42.

The processors 154, 156 and 158 are conventional microprocessors, microcontrollers or digital signal processors, all of which are essentially general purpose computers that have been programmed to perform the specific functions of the electrical electrosurgical generator components 150.

The electrical generator components 150 also include the user input switch devices 32 which allow the user to select the mode of electrosurgical operation (cut, coagulation or a blend of both) and the desired amount of output power. The generator components 150 also include the information output displays 34 and indicators 36. The activation signals 152 are applied from the finger switch 66 and the foot switch 28 to an activation port 176. The system processor 154 reads the activation signals 152 from the activation port 176 to control the output power delivery. The components 32, 34, 36, 38 and 176 are connected to and communicate with the system processor 154 by a conventional input/output (I/O) peripheral bus 178, which is separate from the system bus 160.

In response to the activation signal 152, the system processor 154 signals the control processor 156 to control the high voltage power supply 162, the RF amplifier 164 and the RF output section 166 to supply the appropriate power level and waveform characteristics of electrosurgical output power. The control processor 156 responds accordingly. In addition, the system processor 154 supplies the relay closure signals 100 and 102 to the power distribution circuit 91 (FIG. 2) which is included within the RF output section 166, if monopolar electrosurgical output power is to be delivered. The system processor 154 supplies only the one relay closure signal 100 or 102 appropriate to delivering the output power to the monopolar handpiece or instrument with which the activation signal 152 is associated. The system processor 154 also supplies the relay closure signal 100 or 102 to the monitor processor 158. Of course, if the activation signal 152 indicates that bipolar electrosurgical energy is to be supplied, the system processor 154 supplies a bipolar response signal 184 to the RF output section 166 and to the monitor processor 158, as shown in FIG. 4. The system processor 154 also supplies to the RF output section 166 the identified relay closure signals 100 and 102 or the bipolar response signal, any of which constitute a power delivery command signal.

The current sensors 116, 118, 124 and 126 deliver the current sense signals 120, 122, 132 and 134 from the power distribution circuit 91 (FIG. 2) of the RF output section 166 to the monitor processor 158. The signals 120, 122, 132 and 134 are shown collectively at 186 in FIG. 4. The collective current sensor signals 186 and the relay closure signals 100 or 102 and a bipolar response signal, are thereafter used by the monitor processor 158 to determine proper output power distribution and to detect any malfunction in the output power distribution.

Each of the processors 154, 156 and 158 has the capability to exercise control over the delivery of power from the electrosurgical generator. The monitor processor 158 and the system processor 154 assert enable signals 200 and 202 to an AND logic gate 204. The control processor 156 asserts a drive-defining signal 206 to the logic gate 204. The drive-defining signal 206 is passed through the logic gate 204 and becomes a drive signal 208 for the RF amplifier 40, so long as the enable signals 200 and 202 are simultaneously presented to the logic gate 204. If either the system processor 154 or the monitor processor 158 de-asserts its enable signal 202 or 200 respectively, the logic gate 204 will terminate the delivery of the drive signal 208 and the RF amplifier 164 will cease to deliver monopolar and bipolar drive signals 172 and 174, resulting in terminating the delivery of electrosurgical power from the generator. Because the control processor 156 develops the drive-defining signal 206 to control the output power of the electrosurgical generator, the control processor 156 can simply de-assert the drive-defining signal 206 to cause the electrosurgical generator to cease delivering output power. Thus, any of the processors 154, 156 or 158 has the capability to shut down or terminate the delivery of power from the electrosurgical generator under conditions of significant discrepancies in the delivery of the electrosurgical power from the generator.

The control processor 156 receives an output current signal 212 and an output voltage to 214 from the RF output section 166. The control processor 156 calculates the amount of output power by multiplying the current and voltage signals 212 and 214 to obtain the power output. The monitor processor 158 receives an output current signal 216 and an output voltage signal 218. The output current and voltage signals 216 and 218 are derived independently of the output current and voltage signals 212 and 214 by separate current and voltage sensors. The monitor processor 158 has thus able to perform output power-related calculations to determine performance characteristics of the control processor 156 in delivering the electrosurgical output power.

Figure 5:
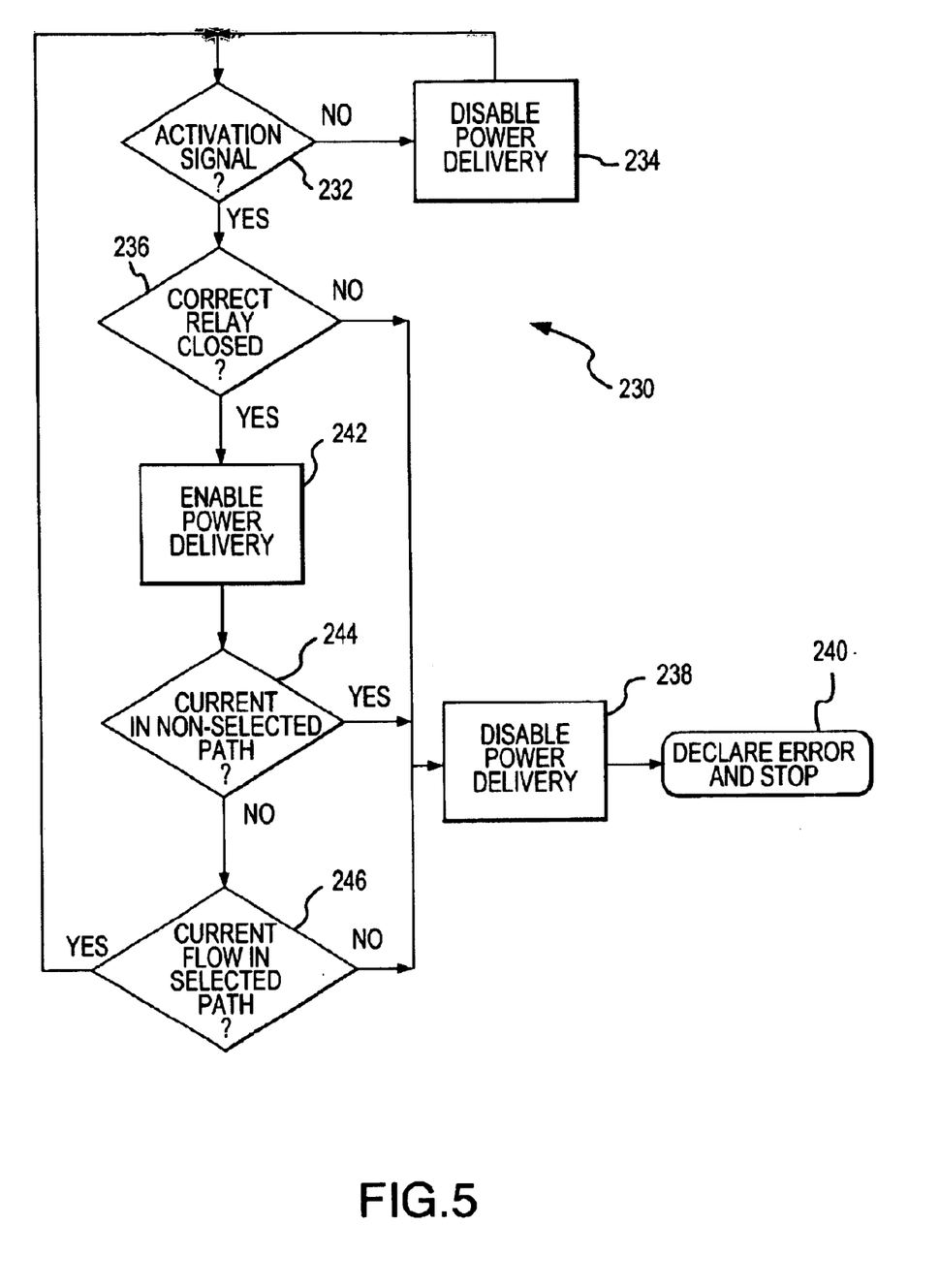
FIG. 5 is a flowchart of functions performed by the electrical components of the electrosurgical generator shown in FIG. 4, to detect an error or malfunction in electrosurgical power delivery.

The basic procedure followed by the monitor processor 158 in making the determination of the proper or improper power distribution is illustrated by the program flow 230 shown in FIG. 5. The program flow 230 remains in a loop established by a negative determination at 232 indicating that no activation signal has been supplied by the system processor 154 (FIG. 4). Without an activation signal, power delivery from the electrosurgical generator is disabled as shown at 234. When an activation signal is asserted, as indicated by an affirmative determination at 232, a further determination is made at 236 as to whether the correct relay (96 or 98, FIG. 4) or the correct switches (not shown) for the delivery of bipolar power (through the conductors 128 and 130, FIG. 4) have been correctly closed. The determination made at step 236 is determined by the monitor processor 158 (FIG. 4) sensing the delivery of the activation relay signals 100 or 102, or sensing the signals (not specifically shown) which results in the conduction of bipolar power through the conductors 128 and 130 (FIG. 2). If the correct relays or switches have not been closed as determined at 236, an error condition is indicated and the program flow proceeds to 238 where the delivery of electrosurgical power is disabled. Thereafter, at 240, an error is declared and the further operation of the electrosurgical generator is terminated.

On the other hand, if the determination at 236 is affirmative, the program flow enables the power delivery at 242. The electrosurgical energy is therefore delivered to the monopolar receptacles 40, 44 and/or 48 or to the bipolar receptacle 42 (FIG. 4), in the manner previously described. Next, at 244, a determination is made whether current is flowing in any non-selected path. Of course, if the determination at 244 is affirmative an error condition is indicated and the power delivery is disabled at 238 and an error is indicated and electrosurgical generator shut down, as shown at 240.

A negative determination at 244 leads to a further determination at 246. At 246, a determination is made as to whether current is flowing in the selected path. Of course, if current is not flowing in the selected path, as determined at 246, an error condition is indicated and the power delivery is disabled at 238, and then an error indication is given along with termination of operation of the generator at 240. On the other hand, if the determination at 246 is affirmative, proper operation of the electrosurgical generator is indicated. The program flow 230 thereafter loops from 246 back to 232 to repeat the process so long as an activation signal at 232 is present.

The determinations made at 244 and 246 are accomplished by using the current sense signals 120, 122, 132 and 134 (FIG. 2) and comparing those signals to the relay activation signals 100 and 102, and the switch activation signals (not shown) which direct the bipolar power through the conductors 128 and 130. Any current sense signal 120, 122, 132 and 134 which indicates current flow in a path where no current flow was intended is an error indication, just as is the case where any current sense signal 120, 122, 132 or 136 indicates no current flow in a path which has been selected.

The program flow 230 illustrates how the present invention may check and evaluate a number of factors that influence the delivery of electrosurgical output power. A first determination is made at 236 as to whether the activation signal from the system processor 154 results in the appropriate relay closure signal 100 or 102 or bipolar current path switch closure. The monitor processor 158 may make an independent determination of whether the appropriate activation signal which the system processor 154 should have delivered to the RF output section 166 is a monopolar or bipolar activation signal, based on information communicated from the system processor 154 to the monitor processor 158 over the system bus 160. This information provides the monitor processor with the ability to determine whether the appropriate relay closure signal has been delivered. The current sense signals 120, 122, 132 and 134 (FIG. 2) provide the monitor processor 158 with the ability to compare whether current is flowing only through the output relay 96 or 98 or bipolar current path which has received the appropriate relay closure signal. These factors should indicate any monopolar output power distribution error or malfunction and permit termination of the delivery of power from the electrosurgical generator under such conditions.

Although the monitor processor 158 has been described as performing the comparisons and correlations, the system processor 154 could also perform these same comparisons and correlations because the information necessary to perform the comparisons and correlations is readily communicated between the two processors 154 and 158 over the system bus 160 or over separate conductors (not specifically shown). In addition, both processors 154 and 158 can separately perform the comparisons and correlations, and then further compare their independently-derived results. Comparing the independently derived results serves as a further check and evaluation on the proper functionality of both processors and the other components of the electrosurgical generator from which the information is derived to make these comparisons. The control processor 156 could also perform or participate in performing the comparisons and correlations, although the control processor 156 will generally be occupied by the process functions of creating and regulating the electrosurgical output power.

The present invention offers the improvement of delivering monopolar and bipolar electrosurgical energy to the appropriate monopolar and bipolar instruments, and detecting a variety of failures, errors, or malfunctions, in the delivery of the electrosurgical energy. The failure detection enables the electrosurgical generator to terminate the delivery of electrosurgical power to prevent risk of injury to the patient, the surgeon or the surgical personnel, as well as to prevent damage to the electrosurgical generator.

Presently preferred embodiments of the invention and its improvements have been described with a degree of particularity. This description has been made by way of preferred example. It should be understood that the scope of the invention is defined by the following claims, which should not be limited by the detailed description of the preferred embodiments set forth above.

What is claimed is:

1. An electrosurgical generator which delivers electrosurgical output power in response to an activation signal, comprising:

an electrosurgical power creation circuit which is operative in response to an enable signal to create the output power;

a delivery path connected to the power creation circuit and through which the output power is delivered from the electrosurgical generator;

a selectively controllable power flow switch connected in the delivery path to conduct the output power through the delivery path in response to an assertion of a power command signal to the power flow switch and to prevent conduction of the output power through the delivery path in response to the de-assertion of the power command signal;

a controller receptive of the activation signal and operative to supply the enable signal to the power creation circuit and to assert the command signal to the power flow switch in response to the activation signal, the controller further operative to withdraw the enable signal from the power creation circuit and to de-assert the command signal to the power flow switch in response to the absence of the activation signal;

a sensor connected in the delivery path to sense the flow of the output power through the delivery path and to assert a sense signal upon sensing the presence of the output power flowing in the delivery path and to de-assert the sense signal upon sensing the absence of the output power flowing in the delivery path; and a detection circuit receptive of the command signal and the sense signal and responsive to an inconsistency in one of the simultaneous assertion of the command and sense signals or the simultaneous de-assertion of the command and sense signals, the detection circuit terminating the supply of the enable signal to the electrosurgical power creation circuit upon detection of the inconsistency.

2. An electrosurgical generator as defined in claim 1, further comprising:

a plurality of the power delivery paths, each of the delivery paths including one power flow switch and one sensor; and wherein:

the detection circuit is receptive of the command and sense signals from each delivery path and responds to an inconsistency in the assertion and de-assertion of the command and sense signals in all of the delivery paths to terminate the enable signal.

3. An electrosurgical generator as defined in claim 2, further comprising:

a processor, and wherein:

the controller and the detection circuit are included within the processor.

4. An electrosurgical generator as defined in claim 2, further comprising:
first and second separate processors which are operatively interconnected with one another; and wherein:
the first processor includes the controller; and
the second processor includes the detection circuit.

5. An electrosurgical generator as defined in claim 4, further comprising:
a third processor which is separate from the first and second processors: and wherein:
the third processor is operatively connected to the first and second processors; and
the third processor is connected to and controls the electrosurgical power creation circuit.

6. An electrosurgical generator as defined in claim 2, wherein:
the power flow switch in one delivery path includes an output relay; and
the power command signal to the power flow switch which includes the output relay comprises a relay closure signal.

7. An electrosurgical generator as defined in claim 6, wherein:
the sensor in the one delivery path which includes the output relay comprises a current sensor to sense current flowing in the one delivery path in response to the delivery of the output power.

8. An electrosurgical generator as defined in claim 6, wherein:
the electrosurgical power creation circuit creates monopolar output power and bipolar output power; and
the monopolar output power is delivered through the delivery path which includes the output relay.

9. An electrosurgical generator as defined in claim 8, wherein:
the bipolar output power is delivered through a bipolar delivery path which is different from the delivery path which includes the output relay;
the electrosurgical power creation circuit includes an output section; and
the power flow switch connected in the bipolar delivery path is included within the output section.

10. A method of determining delivery conditions of output electrosurgical power from an electrosurgical generator in which the electrosurgical power is delivered in response to an activation request for output power, comprising:
selecting one of a plurality of different delivery paths for the delivery of the output power based on the activation request;
delivering output power in response to the activation request;
determining whether the output power delivered is flowing in any delivery path other than the selected delivery path; and
terminating the delivery of output power if the output power is flowing in any delivery path other than the selected delivery path.

11. A method as defined in claim 10, further comprising:
determining whether the output power delivered is flowing in the selected delivery path; and
terminating the delivery of output power upon determining that the delivered output power is not flowing in the selected delivery path.

12. A method as defined in claim 1, further comprising:
determining whether output power is flowing in each of the plurality of delivery paths.

13. A method as defined in claim 12, further comprising:
sensing a flow of current caused by the delivered output power to determine whether electrosurgical energy is flowing in each delivery path.

14. A method as defined in claim 1, wherein the plurality of different delivery paths include a delivery path in which monopolar electrosurgical power flows and a delivery path in which bipolar electrosurgical power flows.

15. A method as defined in claim 1, wherein one of the delivery paths includes an output relay which conducts current caused by the electrosurgical output power upon closure of the output relay, and the method further comprises:
selecting the delivery path which includes the output relay as the delivery path for the delivery or the output power;
applying a relay closure signal to the output relay to close the output relay in response to the activation request; and
determining whether the output relay closed in response to the relay closure signal by sensing current flowing through the delivery path which includes the output relay as a result of delivering the output power.

16. A method as defined in claim 15, further comprising:
terminating the delivery of output power upon determining that the relay closure signal did not result in the flow of delivered output power through the selected delivery path which includes the output relay.

17. A method as defined in claim 16, further comprising:
sensing current flowing in each of the plurality of delivery paths in response to the delivery of the output power;
determining whether current is flowing in any delivery path other than the selected delivery path which includes the output relay; and
terminating the delivery of output power upon determining that the delivered output power is flowing in any delivery path other than the selected delivery path which includes the output relay.

18. A method as defined in claim 15, wherein at least two of the plurality of delivery paths each include an output relay which conducts current caused by the electrosurgical output power upon closure of the output relay associated with the each of those delivery paths, and the method further comprises:
deriving current sense signals indicative of current flowing in each delivery path in which an output relay is included;
determining whether the presence and absence of relay closure signals applied to each output relay correlate with the current sense signals; and
terminating the delivery of output power upon determining the presence and absence of relay closure signals do not correlate with the current sense signals indicating the presence and absence of current flowing in the delivery paths.

19. A method of determining delivery conditions of output electrosurgical power from an electrosurgical generator which has a plurality of delivery paths through which the output power can be delivered, comprising:

delivering the output power in response to an activation request for the delivery of electrosurgical output power;

commanding the delivery of the output power through a selected one of the plurality of delivery paths;

delivering the output power in response to commanding the delivery of the output power;

sensing whether output power is flowing in each of the plurality of delivery paths;

determining whether the delivery path in which output power is flowing correlates with the selected one delivery path;

determining whether each delivery path in which output power is not flowing correlates to a delivery path for which output power delivery has not been commanded;

terminating the delivery of output power upon determining that the delivered output power is not flowing in the selected delivery path; and terminating the delivery of output power upon determining that the delivered output power is flowing in any delivery path other than the selected one delivery path.

20. A method as defined in claim 19, further comprising:

selecting the one delivery path to which to command delivery of the output power in response to the activation request.

21. A method as defined in claim 20, wherein the electrosurgical generator includes first and second processors, and the method further comprises:

executing a procedure on the first processor in response to the activation request to select the one delivery path and to command the delivery of the output power through the selected one path; and executing a procedure on the second processor in response to the command for delivery of the output power through the selected one delivery path and in response to current sensed in the plurality of delivery paths to determine the correlation of flow of output power in the commanded delivery path and the absence of the flow of output power in each delivery path other than the selected one delivery path.

* * * * *

UNITED STATES PATENT AND TRADEMARK OFFICE
CERTIFICATE OF CORRECTION

PATENT NO. : 6,830,569 B2  Page 1 of 1
APPLICATION NO. : 10/300703
DATED : December 14, 2004
INVENTOR(S) : Richard Thompson and Tim Refior It is certified that error appears in the above-identified patent and that said Letters Patent is hereby corrected as shown below:

Column 14
  Line I;
    Change "1" to read --11 --;
  Line 8,
    Change "1" to read --11 --;
  Line 12,
    Change "1" to read --11 --, Signed and Sealed this Ninth Day of January, 2007

JON W. DUDAS
*Director of the United States Patent and Trademark Office*